(12) United States Patent
Bradley

(10) Patent No.: US 7,805,197 B2
(45) Date of Patent: Sep. 28, 2010

(54) SYSTEM AND METHOD USING MULTIPLE TIMING CHANNELS FOR ELECTRODE ADJUSTMENT DURING SET UP OF AN IMPLANTED STIMULATOR DEVICE

(75) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1009 days.

(21) Appl. No.: 11/399,876

(22) Filed: Apr. 7, 2006

(65) Prior Publication Data
US 2007/0239228 A1   Oct. 11, 2007

(51) Int. Cl.
*A61N 1/00*   (2006.01)
(52) U.S. Cl. .......................................................... 607/46
(58) Field of Classification Search ................... 607/46, 607/66, 148, 48, 72, 112, 122, 132
See application file for complete search history.

(56) References Cited

U.S. PATENT DOCUMENTS

| | | | | |
|---|---|---|---|---|
| 3,646,940 A | 3/1972 | Timm et al. | ................. | 128/421 |
| 3,724,467 A | 4/1973 | Avery et al. | ................. | 128/418 |
| 3,822,708 A | 7/1974 | Zilber | .................... | 128/419 R |
| 4,408,608 A | 10/1983 | Daly et al. | .................... | 607/57 |
| 4,424,812 A | 1/1984 | Lesnick | ....................... | 607/30 |
| 5,501,703 A | 3/1996 | Holsheimer et al. | ........... | 607/46 |
| 5,522,865 A | 6/1996 | Schulman et al. | ............. | 607/56 |
| 5,643,330 A | 7/1997 | Holsheimer et al. | ........... | 607/46 |
| 5,702,429 A | 12/1997 | King | ............................ | 607/46 |
| 5,814,092 A | 9/1998 | King | ............................ | 607/46 |
| 5,913,882 A | 6/1999 | King | ............................ | 607/62 |

(Continued)

FOREIGN PATENT DOCUMENTS

EP   0811395   6/1997

(Continued)

OTHER PUBLICATIONS

U.S. Appl. No. 60/670,059, filed Apr. 11, 2005.

(Continued)

*Primary Examiner*—George Manuel
*Assistant Examiner*—Shubatra Narayanaswamy
(74) *Attorney, Agent, or Firm*—Vista IP Law Group LLP

(57) ABSTRACT

Methods using multiple timing channels for electrode adjustment during set up of an implanted stimulator device are disclosed. In one embodiment, at least two conditions of electrodes (i.e., electrode combinations, pulse widths, pulse frequencies, pulse amplitudes) can be "simultaneously" tested by providing each condition in its own timing channel. In a preferred embodiment, the pulses in each of the timing channels are interleaved and non-overlapping to preserve the ability of the patient to assess the therapeutic feel of both and to allow some time between pulses for recovery. As well as allowing two sets of electrode conditions to be gauged at the same time, the technique allows the electrode to be manipulated during set up with ease and with a reduced possibility of providing the patient with erroneous results. For example, the two conditions in the two timing channels can comprise initial and target final conditions, and transitioning between from one to the other during device set up is facilitated as compared to the prior art because concerns with electrodes having inconsistent properties in both conditions are alleviated.

12 Claims, 16 Drawing Sheets

| Chan. | E1 | E2 | E3 | E4 | E5 | E6 | E7 | E8 | E9 | E10 | E11 | E12 | E13 | E14 | E15 | E16 | case |
|---|---|---|---|---|---|---|---|---|---|---|---|---|---|---|---|---|---|
| A | + | | - | + | - | | | | | | | | | | | | |
| B | | | | | - | + | - | | | | | | | | | | |
| C | | | | | | | | | | + | - | | | + | | | |
| D | - | + | | | | | - | | | | | | | | + | | |

168

U.S. PATENT DOCUMENTS

| | | | |
|---|---|---|---|
| 5,941,906 A | 8/1999 | Barreras, Sr. et al. | 607/66 |
| 5,991,663 A | 11/1999 | Irlicht et al. | 607/57 |
| 6,027,456 A | 2/2000 | Feler et al. | 600/554 |
| 6,083,252 A | 7/2000 | King et al. | 607/70 |
| 6,181,969 B1 | 1/2001 | Gord | 607/59 |
| 6,393,325 B1 * | 5/2002 | Mann et al. | 607/46 |
| 6,516,227 B1 | 2/2003 | Meadows et al. | 607/46 |
| 6,609,029 B1 | 8/2003 | Mann et al. | 607/37 |
| 6,741,892 B1 | 5/2004 | Meadows et al. | 607/116 |
| 6,895,280 B2 | 5/2005 | Meadows et al. | 607/46 |
| 6,909,917 B2 | 6/2005 | Woods et al. | 607/46 |
| 6,950,706 B2 | 9/2005 | Rodriguez et al. | 607/46 |
| 2003/0204222 A1 | 10/2003 | Leinders et al. | 607/48 |
| 2004/0034394 A1 | 2/2004 | Woods et al. | 607/46 |
| 2004/0116978 A1 | 6/2004 | Bradley | 607/48 |
| 2004/0215250 A1 | 10/2004 | Augustijn et al. | 607/9 |
| 2005/0004628 A1 | 1/2005 | Goetz et al. | 607/60 |
| 2005/0278001 A1 * | 12/2005 | Qin | 607/48 |
| 2006/0229687 A1 | 10/2006 | Goetz et al. | 607/46 |
| 2006/0259099 A1 | 11/2006 | Goetz et al. | 607/66 |

FOREIGN PATENT DOCUMENTS

| | | |
|---|---|---|
| WO | 02/09808 | 2/2002 |

OTHER PUBLICATIONS

U.S. Appl. No. 11/295,168, filed Dec. 5, 2005, Bradley.

* cited by examiner

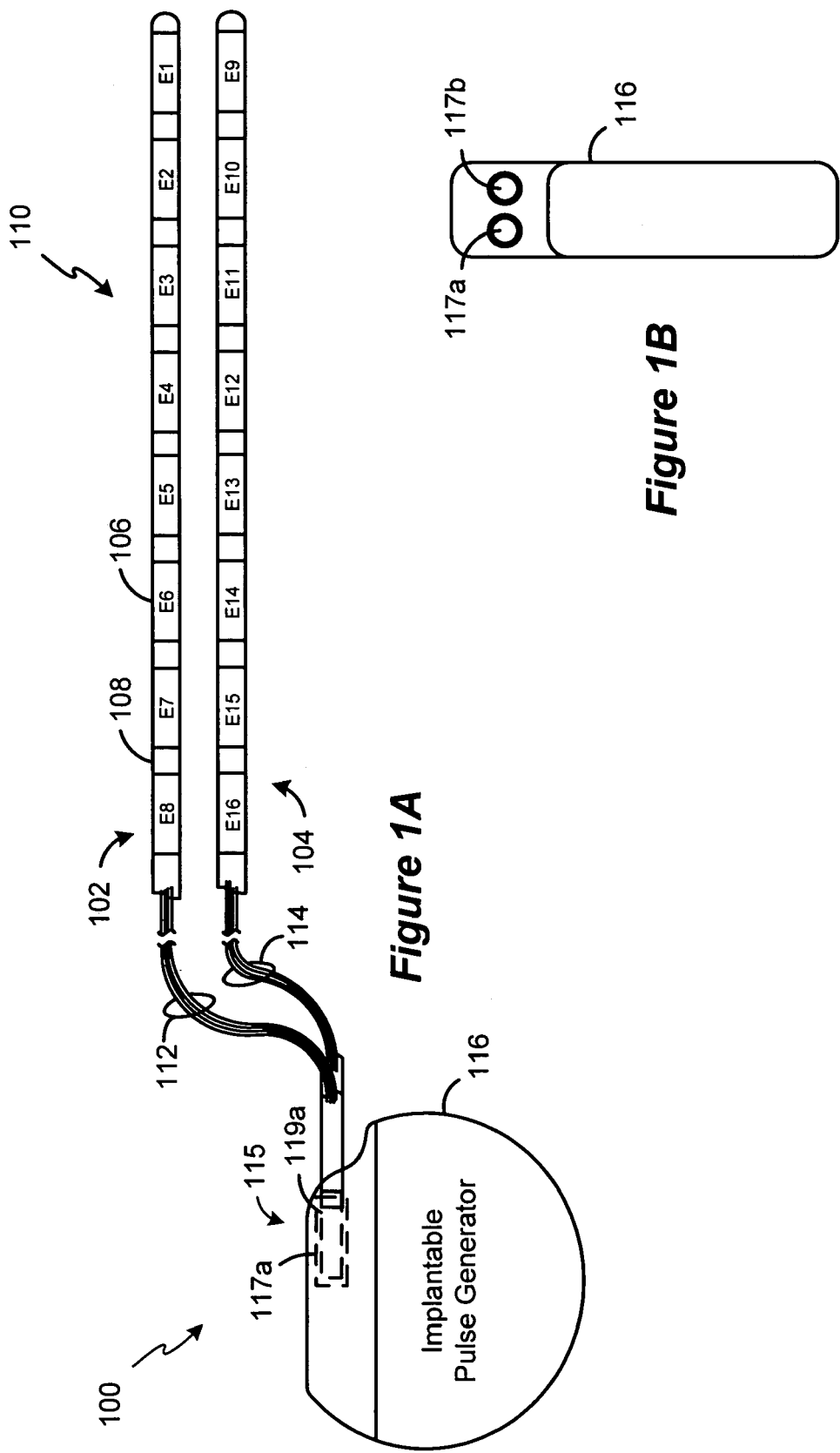
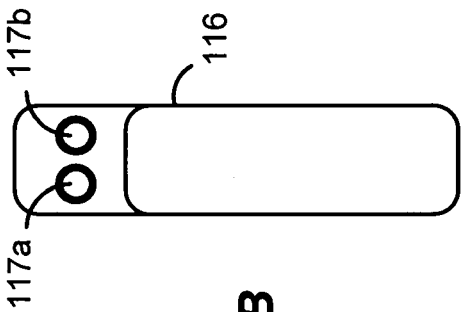
*Figure 1A*
*Figure 1B*

| Chan. | E1 | E2 | E3 | E4 | E5 | E6 | E7 | E8 | E9 | E10 | E11 | E12 | E13 | E14 | E15 | E16 | case |
|---|---|---|---|---|---|---|---|---|---|---|---|---|---|---|---|---|---|
| A | + |   | - | + | - |   |   |   |   |   |   |   |   |   |   |   |   |
| B |   |   |   | - |   | + |   | - |   |   |   |   |   |   |   |   |   |
| C |   |   |   |   |   |   |   |   |   |   | + | - |   |   | + |   |   |
| D | - | + |   |   |   |   |   | - |   |   |   |   |   |   |   | + |   |

SYSTEM AND METHOD USING MULTIPLE TIMING CHANNELS FOR ELECTRODE ADJUSTMENT DURING SET UP OF AN IMPLANTED STIMULATOR DEVICE

FIELD OF THE INVENTION

The present invention relates to therapeutic electrical stimulation systems and methods and, more specifically, relates to adjusting electrodes during set up of an implanted stimulator device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

Spinal cord stimulation is a well-accepted clinical method for reducing pain in certain populations of patients. As shown in FIGS. 1 and 2, a Spinal Cord Stimulation (SCS) system typically includes an Implantable Pulse Generator (IPG) or Radio-Frequency (RF) transmitter and receiver 100 (collectively, "IPGs"), at least one electrode lead 102 and/or 104 having a plurality of electrodes 106, and, optionally, at least one electrode lead extension 120. The electrodes 106 are arranged in a desired pattern and spacing on the lead(s) 102, 104 to create an electrode array 110. Wires 112, 114 within one or more leads(s) 102, 104 connect each electrode 106 in the array 110 with appropriate current source/sink circuitry in the IPG 100.

In an SCS application, the electrodes lead(s) 102, 104 with the electrodes 106 are typically implanted along the spinal cord 19 (FIG. 2B), and the IPG 100 generates electrical pulses that are delivered through the electrodes 106 to the nerve fibers within the spinal column. The IPG 100 body itself is normally implanted in a subcutaneous pocket, for example, in the patient's buttocks or abdomen. The electrode lead(s) 102, 104 exit the spinal column and generally attach to one or more electrode lead extensions 120 (FIG. 2), which in turn are typically tunneled around the torso of the patient to the subcutaneous pocket where the IPG 100 is implanted. Alternatively, if the distance between the lead(s) 102, 104 and the IPG 100 is short, the electrode lead(s) 102, 104 may directly connect with the IPG 100 without lead extensions 120. For examples of other SCS systems and other stimulation system, see U.S. Pat. Nos. 3,646,940 and 3,822,708, which are hereby incorporated by reference in their entireties. Of course, an IPG 100 is an active device requiring energy for operation, which may be provided by an implanted battery or an external power source.

Precise placement of the lead(s) 102, 104 relative to the target nerves is important for achieving a satisfactory physiological response, and for keeping stimulation thresholds low to conserve battery power. A conventional lead implantation procedure commonly places the leads 102, 104 parallel to the spinal cord column 19 at or near the physiological midline 91, as is shown in respective perspective and cross-sectional views in FIGS. 3A and 3B. More particularly, and as best shown in FIG. 3B, the electrode leads 102, 104 are placed directly on the dura mater 51 within the epidural space 70. (Cerebro-spinal fluid 72 is between the electrode array 110 and the white matter 52 of the spinal cord 19. Dorsal root nerves 50 are shown emanating from grey matter 53). When the leads 102, 104 are placed on opposite sides of the physiological midline 91 as shown, additional flexibility is provided in the ability to recruit (i.e., stimulate) nerves in the dorsal column, and to treat symptoms manifesting on either the left or right sides of the patient's body.

In addition to precise placement of the electrode array, proper selection of the electrodes, i.e., determining which of the electrodes 106 in the array should be active in a given patient, is critical for achieving effective stimulation therapy. However, because of the uncertainties of the distances of the electrodes from the neural target, the unknown nature of the specific conductive environment in which the electrode is placed, etc., it generally cannot be known in advance and with precision which combination of active electrodes will be perceived by a patient as providing optimal therapy. As a result, patient therapy generally requires at the outset that various electrode combinations be tried and feedback received from the patient as to which of the combinations feels most effective from a qualitative standpoint, what is referred to herein as IPG "set up."

Various electrode combinations and other stimulation parameters can be tried during set up by programming the IPG 100, for example using the clinician programmer 204 or a hand-held programmer 202 (see FIG. 7, discussed below). For example, and as best visualized in FIG. 3A, the IPG 100 can be programmed such that electrode E1 comprises an anode (source of current), while E2 comprises a cathode (sink of current). Or, the IPG 100 can be programmed such that electrode E1 comprises an anode, while E9 comprises a cathode. Alternatively, more than one electrode can be used in both the sourcing and sinking of current. For example, electrode E1 could comprise an anode, while both E2 and E9 can comprise cathodes. Of course, the amount of current sourced or sunk can also be programmed by the IPG 100. Thus, in the last example, electrode E1 could sink 5 mA, while electrode E2 sources 4 mA and electrode E9 sources 1 mA. The frequency of electrode stimulation pulses, as well as the pulsewidth of such stimulation pulses, is also programmable.

Ultimately, which electrodes are activated by the IPG 100, and the polarities (cathode v. anode) and magnitudes (amount of current) of those activated electrodes, are based largely on patient feedback during IPG set up as noted earlier. Thus, the patient, usually with the benefit of a clinician, will experiment with the various electrode settings, and will report relative levels of comfort and therapeutic effectiveness to arrive at electrode settings that are best for a given patient's therapy.

Generally, and as one skilled in the art will appreciate, cathodic stimulation across the dorsal column (e.g., across the physiological midline 91) is preferable to cathodic stimulation across the dorsal roots 50. What this means in FIG. 3A is that cathodic stimulation from left to right (which promotes recruitment of the dorsal column) is generally preferable to cathodic stimulation from top to bottom (which promotes recruitment of the dorsal roots 50). In other words, generally, it is preferable to activate, for example, electrodes E1 and E9 (left to right, or from lead 102 to lead 104) as cathodic sinks as compared to electrode E1 and E2 (top to bottom, or along either lead 102 or 104 individually). This being said, this is merely a preference and not an inviolable rule, as ultimately which contacts are activated is a matter of patient's subjective preference.

In the prior art, patients and/or clinicians used a technique called "field steering" or "current steering" to try and simplify the iterative process for determining a patient's optimal electrode settings during set up of the IPG. See U.S. Pat. No. 6,909,917, which is incorporated herein by reference in its entirety. In current steering, the current sourced or sunk by the electrodes is gradually redistributed by the patient or clinician to different electrodes using a single stimulation timing channel. Such steering can be facilitated using some sort of user interface associated with an external programmer 202 or 204, such as a joystick or other directional device 206 (see FIG. 7). Examples of current steering are shown in FIGS. 4 and 5. Starting first with FIG. 4, assume that the IPG 100 has certain initial conditions, namely that electrode E1 has been programmed to source 10 mA of current, while electrode E9 has been programmed to sink 10 mA of current. This initial condition might be arrived at after some degree of experimentation, and might be a condition at which the patient is feeling a relatively good response, but a response which has not yet been fully optimized.

In an attempt at further optimization, current steering can commence from these initial conditions. Thus, in FIG. 4, suppose electrode E1 is selected and the current sourced from that electrode is to be moved downward (e.g., by clicking downward on the joystick). As shown, this moves 2 mA of sourcing current from electrode E1 (8 mA) to electrode E2 (2 mA). Another downward click moves another 2 mA, so that now E1 sources 6 mA and E2 sources 4 mA. Selection of sink electrode E9, followed by yet another downward click moves 2 mA of sink current to electrode E10 as shown. Current steering may also occur from left to right, i.e., from between leads 102 and 104. For example, it can be seen in the last step of FIG. 5 that 2 mA of source current has been steered from electrode E2 to electrode E10.

Gradual steering of the current in this manner (e.g., in increments) is generally considered advisable to safeguard against abrupt changes of the stimulation field which may be uncomfortable or dangerous for the patient. For example, assume from the initial condition in FIG. 4 that the patient feels relatively good coverage. If this is the case, it might be useful to try moving the cathode around, from E9 to either E2 or E10 for example, to see if even better coverage could be afforded the patient. However, it would generally be unadvisable to abruptly put the entirety of electrode E9's sink current (–10 mA) onto electrodes E2 or E10. Even though these electrodes are physically close to electrode E9, to place the full sink current onto these electrodes could have unforeseen and undesirable effects. Different nerves would certainly be affected by such a change in electrode activation, and it is not necessarily known how moving the full sink current would affect those nerves. If the current when applied to the new electrodes (e.g., E2 or E10) is too low (i.e., sub-threshold), no clinical response would be noticed, even if the electrodes were ultimately suitable choices. If the current is too high (i.e., supra-threshold), the result might be painful (or dangerous) for the patient. Accordingly, incremental movement of the current was considered the best approach.

However, such current steering, particularly in increments, has drawbacks. For example, consider the hypothetical shown in FIG. 6. Suppose initially that the patient perceives good coverage from the initial condition depicted in FIG. 6A, in which the active electrodes are tightly clustered along one lead 102. As shown, electrodes E1 and E3 each provide a 5 mA source current, while the middle electrode, E2 sinks the sum of that current, 10 mA. These initial conditions may suggest that a relatively similar combination of electrodes, but shifted by one electrode (E2-E4), would be reasonable to try as a target final condition, as shown in FIG. 6B. Not only may such shifting of electrodes be advisable during set up of the IPG 100, such adjustment may be necessary in an once-previously-optimized system should the lead 102 or 104 longitudinally slip along the spinal column 19 due to patient physical activity.

In any event, for whatever reason, it may be reasonable to simply try applying the conditions on electrodes E1-E3 on electrodes E2-E4. Using the current steering technique of the prior art, and recognizing the advisability of incremental steering of current between electrodes, the result of moving the conditions of electrodes E1-E3 to electrodes E2-E4 is slow and subject to erroneous results. Thus, as is illustrated in the sequential steps of FIG. 6C, the settings for the electrodes had to be incrementally "inch-wormed" into their new positions. Thus, the conditions at electrode E3 are first moved to E4 over a series of incremental steps. This is necessary to free electrode E3 to receive new settings, because E3 can't simultaneously respond to its old and new settings, i.e., electrode E3 cannot simultaneously source and sink anodic and cathodic current, respectively. Then, once E3 is free, E2's conditions are incrementally moved to E3. Then, once E2 is free, E1 is moved to E2 in like fashion. Thus, many steering steps are required to fully move the initial conditions on electrode E1-E3 to electrodes E2-E4. If nothing else, this is time consuming and cumbersome.

More importantly, this method of steering the current during set up in the hypothetical example of FIG. 6C can be subject to erroneous results. Suppose that the initial conditions (FIG. 6A) are a reasonable starting point for a particular patient, but that the target final conditions (FIG. 6B) would be even better for the patient. Because the prior art steering technique requires many intermediary steps between the initial conditions and the desired final conditions, it is possible that these intermediary steps could inadvertently dissuade the patient from discovering the benefits of the target final conditions. For example, notice that in the intermediary steps, all four electrodes E1-E4 are utilized to varying degrees. These intermediary steps do not necessarily bear a good relation to either the initial conditions (generally good) or the final conditions (even better). For example, in intermediary step 111a, electrode E3 draws no current at all, although in the final condition E3 should be drawing all of the sink current (10 mA). It is therefore not surprising that intermediary step 111a might not feel optimal for the patient. Specifically, the patient may find the intermediary steps uncomfortable, or the patient may not feel any stimulation effect or therapeutic relief whatsoever. In short, there is a risk that if the intermediary conditions are not perceived by the patient or clinician during set up as steps taken in the "right direction" towards more effective electrode settings, the plan to move the settings to the final conditions may be abandoned, even though with patience it would have been advisable to continue implementing this plan.

Moreover, because in the particular example of FIG. 6C the cathodic shifting occurs up and down along the lead, the negative effect of non-optimal intermediary conditions is potentially exacerbated. This is because movement of the cathode up and down a particular lead will tend to recruit different dorsal roots 50. As noted above, it is generally not preferred to stimulate the spinal column in this manner.

Accordingly, what is needed is an improved method for optimizing electrode activation during the set up of an implantable stimulator device, and this disclosure provides embodiments of such a solution.

SUMMARY

Methods using multiple timing channels for electrode adjustment during set up of an implanted stimulator device are disclosed. In one embodiment, at least two conditions of electrodes (i.e., electrode combinations, pulse widths, pulse frequencies, pulse amplitudes) can be "simultaneously" tested by providing each condition in its own timing channel. In a preferred embodiment, the pulses in each of the timing channels are interleaved and non-overlapping to preserve the ability of the patient to assess the clinical effect of both channels independently and to allow some time between pulses for recovery. As well as allowing two sets of electrode conditions to be gauged at the same time, the technique allows the electrode to be manipulated during set up with ease and with a reduced possibility of providing the patient with erroneous results. For example, the two conditions in the two timing channels can comprise initial and target final conditions, and transitioning between from one to the other during device set up is facilitated as compared to the prior art because concerns with electrodes having inconsistent properties in both conditions are alleviated.

BRIEF DESCRIPTION OF THE DRAWINGS

The above and other aspects of the present invention will be more apparent from the following more particular description thereof, presented in conjunction with the following drawings, in which:

FIGS. 1A and 1B show an electrode array and the manner in which it is coupled to the implantable stimulator device in a SCS.

FIG. 11 shows an example of various timing channels usable in an implantable stimulator device, and shows whether each electrode in a channel operates as a source or sink of current.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing schemes for the adjustment of active electrodes during IPG set up that are the focus of this disclosure, the circuitry, structure, and function of an implantable stimulator device in which the technique can be used is set forth for completeness.

The disclosed implantable stimulator device may comprise an implantable pulse generator (IPG) or similar electrical stimulator and/or electrical sensor that may be used as a component of numerous different types of stimulation systems. More specifically, the description that follows relates to use of the invention within a spinal cord stimulation (SCS) system as an exemplary embodiment. However, it is to be understood that the invention is not so limited. Rather, the invention may be used with any type of implantable electrical circuitry that could benefit from the disclosed technique. For example, the present invention may be used as part of a system employing a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc. Moreover, the technique can be used in non-medical and/or non-implantable systems as well.

Figure 7:
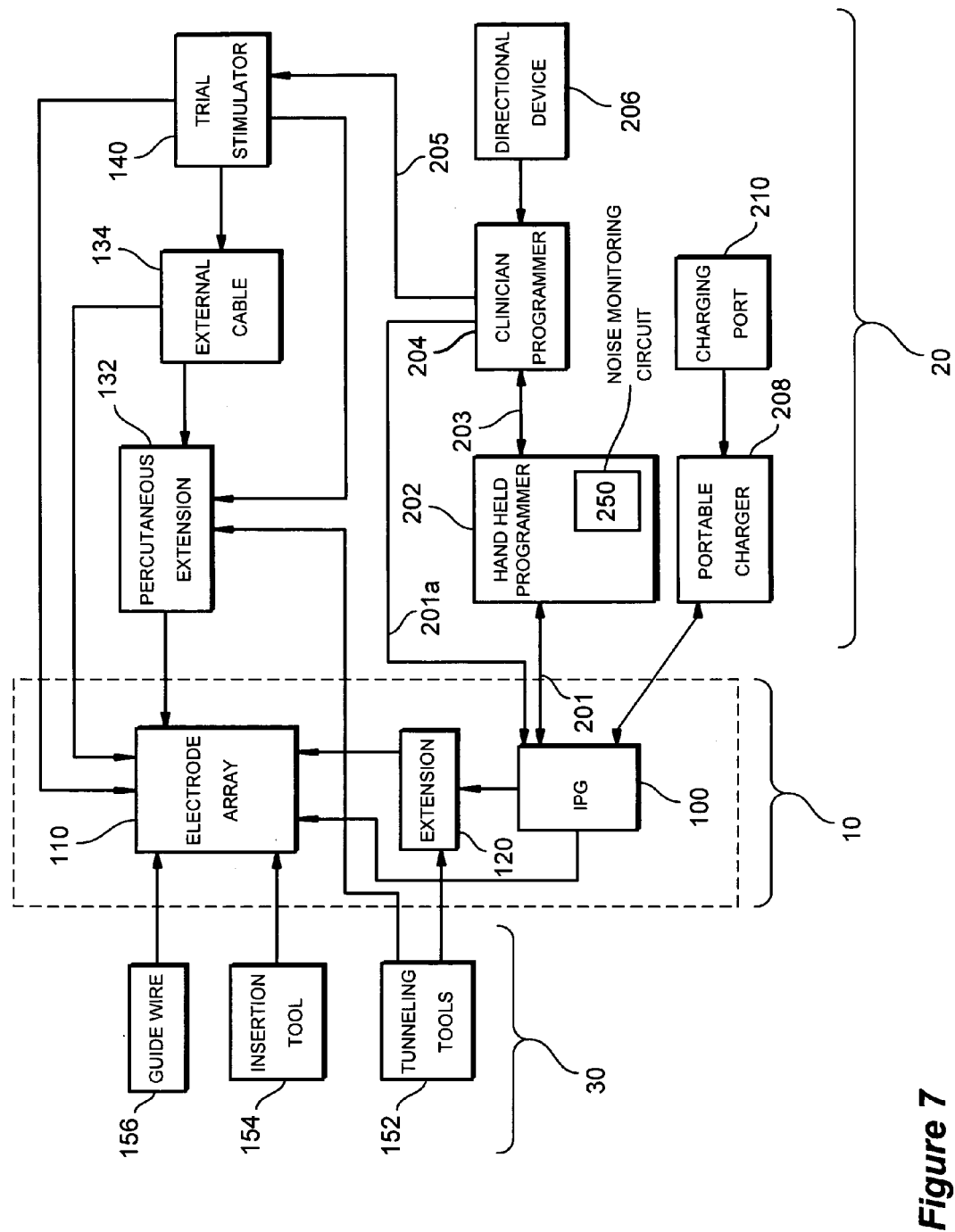
FIG. 7 shows a block diagram illustrating exemplary implantable, external, and surgical components of a spinal cord stimulation (SCS) system in which the present invention can be used.

Turning first to FIG. 7, a block diagram is shown that illustrates the various components of an exemplary SCS system in which the invention may be used. These components may be subdivided into three broad categories: implantable components 10, external components 20, and surgical components 30. As seen in FIG. 7, the implantable components 10 include an implantable pulse generator (IPG) 100, an electrode array 110, and (as needed) a lead extension 120 as described earlier. In an exemplary embodiment, the IPG 100, described more fully below, may comprise a rechargeable, multi-channel, telemetry-controlled, pulse generator housed in a rounded high-resistivity titanium alloy case 116 (FIG. 1A) to reduce eddy current heating during the inductive charging process.

Figure 8:
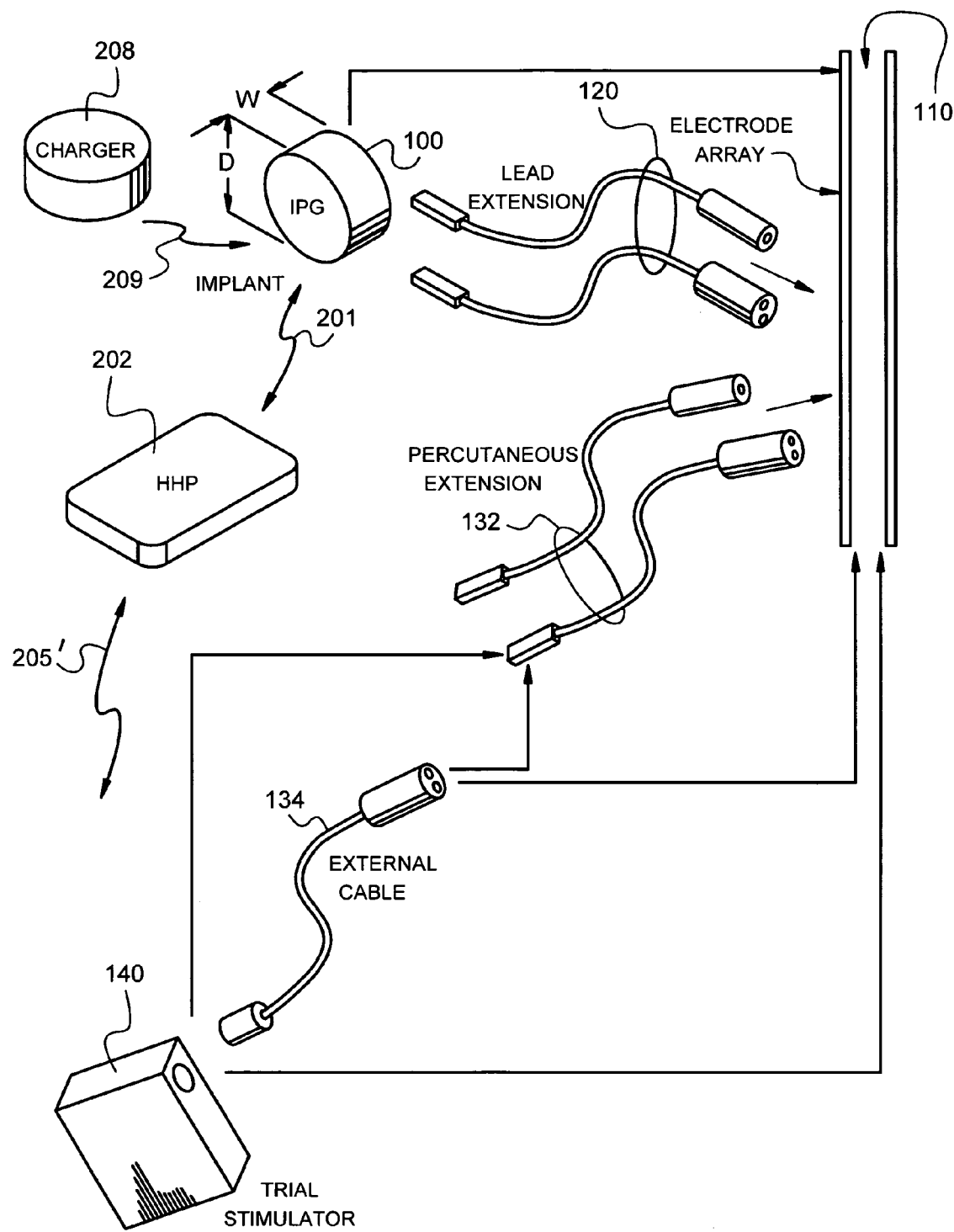
FIG. 8 shows various components of the SCS system of FIG. 8.

As seen best in FIG. 8, and as also illustrated in FIG. 7, the electrode array 110 and its associated lead system typically interface with the implantable pulse generator (IPG) 100 via the lead extension system 120. The electrode array 110 may also be connected to an external trial stimulator 140, through the use of a percutaneous lead extension 132 and/or an external cable 134. The external trial stimulator 140 typically includes the same or similar pulse generation circuitry as does the IPG 100, and is used on a trial basis, e.g., for 7-10 days, after the electrode array has been implanted and prior to implantation of the IPG 100, to test the effectiveness of the stimulation that is to be provided.

Referring again to FIGS. 7 and 8, and as noted earlier, a hand-held programmer (HHP) 202 may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set by a patient or clinician within prescribed limits during set up. The HHP 202 may also be linked with the external trial stimulator 140 through another link 205', e.g., an infra red link. Detailed programming of the IPG 100 is preferably accomplished through the use of an external clinician's programmer (CP) 204 (FIG. 7), which may also be hand-held and which may be coupled to the IPG 100 directly via link 2011a or indirectly through the HHP 202. An external charger 208, non-invasively coupled with the IPG 100 through link 209, e.g., an inductive link, allows energy stored or otherwise made available to the charger 208 to be coupled into the rechargeable battery housed within the IPG 100.

FIGS. 1A and 1B show the electrode array 110 and the manner in which it is coupled to the IPG 100. As shown, the electrode array 110 comprises first and second implantable leads 102 and 104 as described earlier. Leads 102 and 104 are in-line leads, meaning that both consist of a plurality of in-line electrodes 106. The electrodes are carried on a flexible body 108. In the illustrated embodiment, there are eight electrodes on lead 102, labeled E1-E8, and eight electrodes on lead 104, labeled E9-E16. The actual number of leads and electrodes will, of course, vary according to the intended application and should not be understood in any limiting sense. As discussed above, leads 102 and 104 may be implanted into a desired location, such as adjacent to the patient's spinal column, through the use of an insertion needle or other conventional techniques.

Each of the electrodes 106 on lead 102 are electrically connected to the IPG 100 by a first signal wire 112 that extends through, or is imbedded in, the associated flexible body 108. Similarly, each of the electrodes 106 on the lead 104 are electrically connected to the IPG 100 by second signal wires 114. The signal wires 112 and 114 and/or the lead extension 120 are connected to the IPG 100 by way of an interface 115. The interface 115 may be any suitable device that allows the leads 102 and 104 and/or lead extension 120 to be removably connected to the IPG 110. Interface 115 may comprise, for example, an electromechanical connector arrangement including lead connectors 117a and 117b (FIG. 1A) configured to mate with corresponding connectors (only connector 119a is shown) on the leads 102 and 104. Alternatively, the leads 102 and 104 can share a single connector that mates with a corresponding connector on the IPG 100. Exemplary connector arrangements are disclosed in U.S. Pat. Nos. 6,609,029 and 6,741,892, which are incorporated herein by reference. Although the electrode array is shown as having two in-line leads 102, 104 each with a plurality of electrodes 106 (e.g., 8 each), it should be understood that more or fewer leads could be used. For example, a single in-line lead with 16 linearly-arranged electrodes 106 could be used as well.

Typically, the IPG 100 is placed in a surgically-made pocket as described earlier, but of course may also be implanted in other locations of the patient's body. Once implanted, the IPG 100 is detachably connected to the lead system, comprising the lead extension 120, if needed, and the electrode array 110. Once implanted and any trial stimulation period is complete, the electrode array 110 and lead extension 120 are intended to be permanent. In contrast, the IPG 100 may be replaced when its power source fails or for other reasons.

Figure 9:
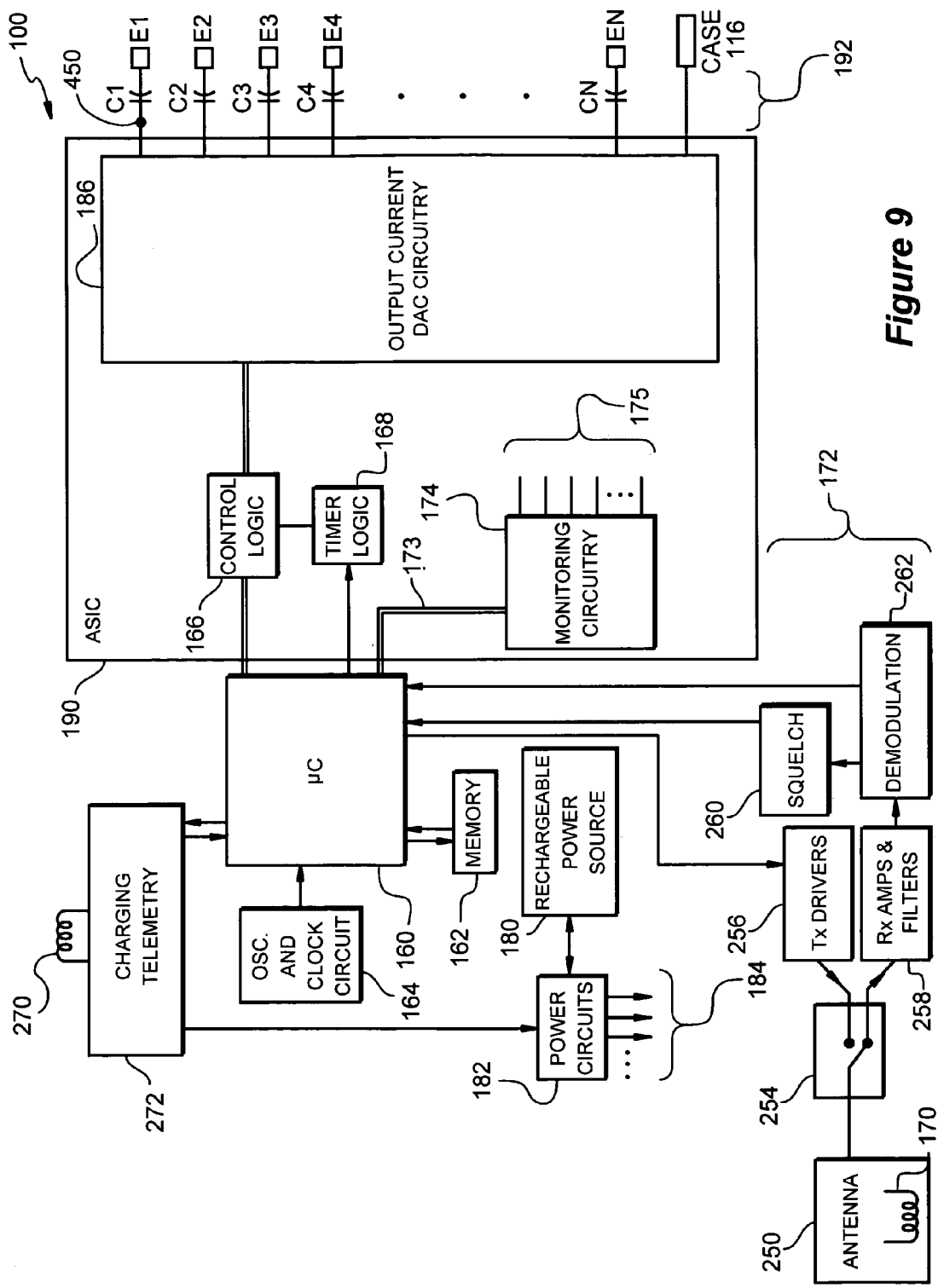
FIG. 9 shows a block diagram illustrating the main components of one embodiment of an implantable stimulator device in which the invention can be used.

Turning next to FIG. 9, a block diagram is shown that illustrates the main components of one embodiment of an implantable pulse generator (IPG) 100 in which embodiments of the invention may be used. As seen in FIG. 9, the IPG includes a microcontroller (IC) 160 connected to memory circuitry 162. The µC 160 typically comprises a microprocessor and associated logic circuitry which in combination with control logic circuits 166, timer logic 168, and an oscillator and clock circuit 164, generate the necessary control and status signals to allow the µC 160 to control the operation of the IPG in accordance with a selected operating program and stimulation parameters.

The operating program and stimulation parameters are telemetered to the IPG 100, where they are received via antenna 250 (which may include a coil 170 and/or other antenna components), processed, e.g., via RF-telemetry circuitry 172, and may be stored, e.g., within the memory 162. The RF-telemetry circuitry 172 demodulates the signal it receives from the HHP 202 or CP 204 to recover the operating program and/or the stimulation parameters. More specifically, signals received by the antenna 250 are passed through the transmit/receive switch 254 to amplifiers and filters 258. From there, the received signals are demodulated (262) using Frequency Shift Keying (FSK) demodulation for example, and the data is then sent to the microcontroller 160 for processing and/or eventual storage. When RF-telemetry circuitry 172 is used to transmit information to the HHP 202 or CP 204 to report in some fashion on its status, the microcontroller 160 sends relevant data to transmission drivers 256, where the carrier is modulated by the data and amplified for transmission. The transmit/receive switch 254 would then be set to communicate with the transmission drivers 256, which in turn drive the data to the antenna 250 to be broadcast.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes E1 ... EN, and the like. Informational data sensed through the monitoring circuit 174 may be sent to a remote location external to the IPG (e.g., a non-implanted location) through telemetry circuitry 172 via coil 170.

The operating power for the IPG 100 may be derived from a rechargeable power source 180, which may comprise a lithium-ion or lithium-ion polymer battery, for example. The rechargeable battery 180 provides an unregulated voltage to power circuits 182. The power circuits 182, in turn, generate the various voltages 184, some of which are regulated and some of which are not, as needed by the various circuits located within the IPG 100. In a preferred embodiment, the battery 180 is charged by an electromagnetic field created by an external portable charger 208 (FIG. 7). When placed near the IPG 100 (e.g., centimeters away), an electromagnetic field emanating from the portable charger 208 induces a current in charging coil 270 (even through a patient's skin). This current is then rectified and regulated to charge the battery 180. Further associated with the charging circuitry is charging telemetry circuitry 272, which is used for example by the IPG 100 to report back to the portable charger 208 when the battery is full, and thus when portable charger can be shut off.

In one exemplary embodiment, any of the N electrodes may be assigned to up to k possible groups or "timing channels." In one preferred embodiment, k may equal four. Moreover, any of the N electrodes can operate, or be included in, any of the k timing channels. The timing channel identifies which electrodes are selected to synchronously source or sink current to create an electric field in the tissue to be stimulated. Pulse amplitudes (e.g., current, although an IPG may also put out a constant voltage pulse) and pulse frequency of electrodes on a timing channel may vary, e.g., as controlled by the HHP 202 and/or the CP 204.

For example, as shown in FIG. 11, four timing channels are defined, and represent groups of electrodes that will be activated as either sources or sinks at a particular time. Thus, in a first timing-channel A, electrodes E1 and E4 will act as current sources (denoted by the plus symbol), while electrodes E3 and E5 will act as sinks (denoted by the minus symbol). Electrodes without any designator in FIG. 11 are not activated and do not participate in the sourcing or sinking of current. By designating different timing channels in this manner, the stimulation provided to the patient can be freely varied with desired therapeutic effect. See U.S. Pat. No. 6,895,280, which is incorporated herein by reference in its entirety. Note that the case 116 (FIG. 1A) of the IPG 100 can also operate as an electrode which can source or sink current. This allows the IPG to be operated in any number of different modes, e.g., a monopolar mode (one electrode EX active with an active case), a bipolar mode (two electrodes EX active), or a multipolar mode (more than two electrodes EX active).

Ultimately, the grouping of the electrodes into different timing channels is managed by the control logic 166 (FIG. 9), with the timing of the activation of the various electrodes in each channel being handled by the timer logic 168. The control logic 166, receiving commands from the microcontroller 160, further sets the amplitude of the current pulse being sourced or sunk to or from a given electrode. Such current pulse may be programmed to one of several discrete current levels, e.g., between 0 to 10 mA in steps of 0.1 mA. The pulse width of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 1000 Hz. Other programmable features can include slow start/end ramping, burst stimulation cycling (on for X time, off for Y time), and open or closed loop sensing modes.

The stimulation pulses generated by the IPG 100 may be charge balanced. This means that the amount of positive/negative charge associated with a given stimulus pulse is offset with an equal and opposite negative/positive charge. Charge balance may be achieved through coupling capacitors CX, which provide a passive capacitor discharge that achieves the desired charge-balanced condition. Alternatively, active biphasic or multi-phasic pulses with positive and negative phases that are balanced may be used to achieve the needed charge balanced condition.

As shown in FIG. 9, much of circuitry included within the IPG 100 may be realized on a single application specific integrated circuit (ASIC) 190. This allows the overall size of the IPG 100 to be quite small, and readily housed within a suitable hermetically-sealed case 116 (FIG. 1A). The IPG 100 may include feedthroughs to allow electrical contact to be individually made from inside of the hermetically-sealed case with the N electrodes that form part of the lead system outside of the case, as was discussed above with reference to FIG. 1.

The telemetry features of the IPG 100 allow the status of the IPG to be checked as noted earlier. For example, when the HHP 202 and/or the CP 204 initiate a programming session with the IPG 100 (FIG. 7), the capacity of the battery is telemetered so that the external programmer can calculate the estimated time to recharge. Any changes made to the current stimulus parameters are confirmed through back-telemetry, thereby assuring that such changes have been correctly received and implemented within the implant system. Moreover, upon interrogation by the external programmer, all programmable settings stored within the implant system 10 may be uploaded to one or more external programmers.

Figure 10:
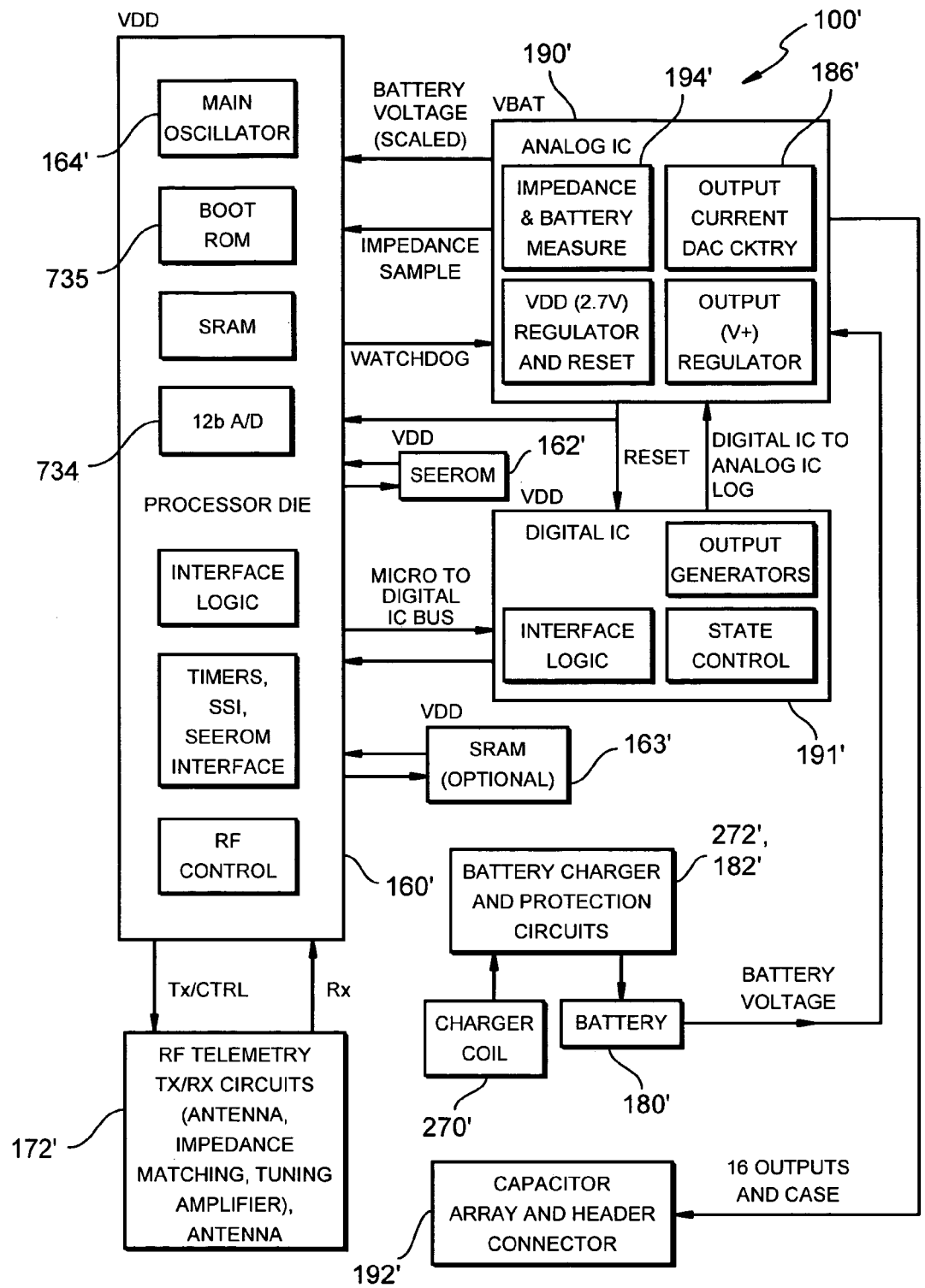
FIG. 10 shows a block diagram illustrating another embodiment of an implantable stimulator device in which the invention can be used.

Turning next to FIG. 10, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 9. The IPG 100' includes a processor die, or chip, 160', an RF telemetry circuit 172' (typically realized with discrete components), a charger coil 270', a rechargeable battery 180', battery charger and protection circuits 272', 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, SRAM or other memory, two synchronous serial interface circuits, a serial EEPROM interface, and a ROM boot loader 735. The processor die 160' may further include an efficient clock oscillator circuit 164', and (as noted earlier) mixer and modulator/demodulator circuitry implementing the QFAST RF telemetry method. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include output current DAC circuitry 186' configured to supply current to a load, such as tissue, for example. The output current DAC circuitry 186' may be configured to deliver up to 20 mA aggregate and up to 12.7 mA on a single timing channel in 0.1 mA steps. However, it will be noted that the output current DAC circuitry 186' may be configured to deliver any amount of aggregate current and any amount of current on a single timing channel, according to one exemplary embodiment.

Regulators for the IPG 100' supply the processor and the digital sequencer with a voltage. Digital interface circuits residing on the analog IC 190' are similarly supplied with a voltage. A programmable regulator supplies the operating voltage for the output current DAC circuitry 186'. The coupling capacitors CX and electrodes EX, as well as the remaining circuitry on the analog IC 186', may all be housed within the hermetically sealed case of the IPG 100. A feedthrough pin, which is included as part of the header connector 192', allows electrical connection to be made between each of the coupling capacitors CN and the respective electrodes E1, E2, E3, . . . , or E16.

The digital IC (DigIC) 191' functions as the primary interface between the processor 160' and the output current DAC circuitry 186', and its main function is to provide stimulus information to the output current DAC circuitry 186'. The DigIC 191' thus controls and changes the stimulus levels and sequences when prompted by the processor 160'. In an exemplary embodiment, the DigIC 191' comprises a digital application specific integrated circuit (digital ASIC).

With the basic structure of an implantable stimulator understood, focus now shifts to a detailed description of the multi-channel electrode adjustment techniques that are the focus of this disclosure.

Embodiments of the present invention take advantage of a feature present in some implantable stimulator devices, namely multiple timing channels. While multiple timing channels have been recognized as useful in the context of providing improved stimulation during actual useful therapeutic operation of the implantable stimulator, (see [CITE], which are incorporated herein by reference in their entireties), it is not believed that multiple timing channels have been used during set up of the IPG, i.e., prior to actual useful therapeutic operation.

Figure 12:
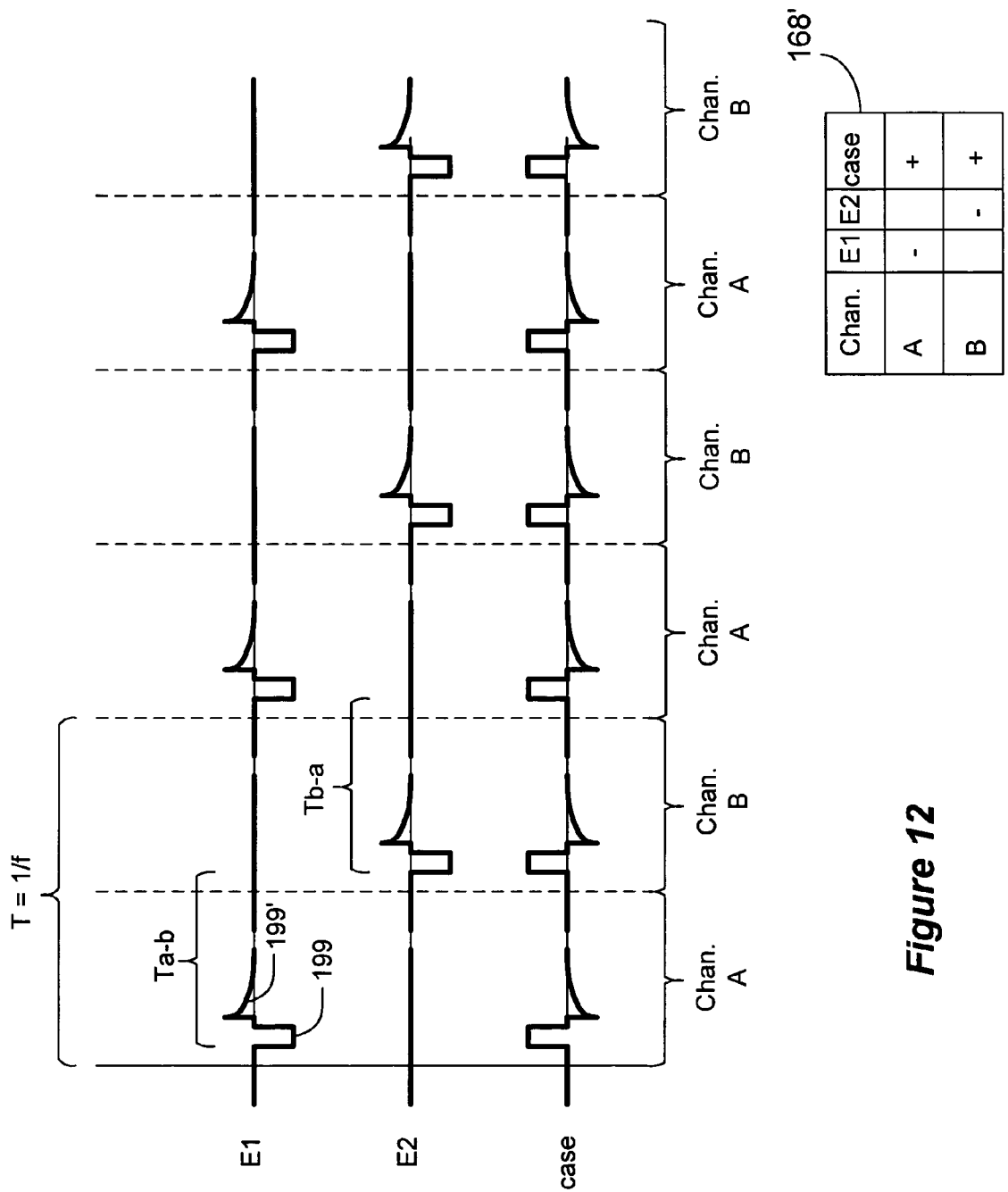
FIG. 12 shows a timing diagram according to an embodiment of the invention in which two or more timing channels are used during IPG set up to stimulate different electrodes in an interleaved fashion.

One basic implementation of using multiple timing channels during set up is illustrated in a simple example with reference to FIG. 12. In this example, two different timing channels are used during IPG set up, A and B. As can be seen, timing channel A activates electrode E1 as the cathode (current sink) and the case of the IPG 100 as the anode (current source). Timing channel B activates electrode E2 as the cathode and the case as the anode. Of course, the timing channels A and B will, in addition to active electrodes, also specify other stimulation parameters pertinent to the channel, such as pulse width (W), pulse amplitude (A), and pulse frequency (f). The timing channels may also specify the nature of charge recovery 199' (active or passive) to occur after each stimulation pulse 199. Charge recovery is well known in the art of implantable stimulators and requires no further elaboration, other than to note in FIG. 12 that passive charge recovery 199' is shown for illustrative purposes only.

Figures 2A, 2B:
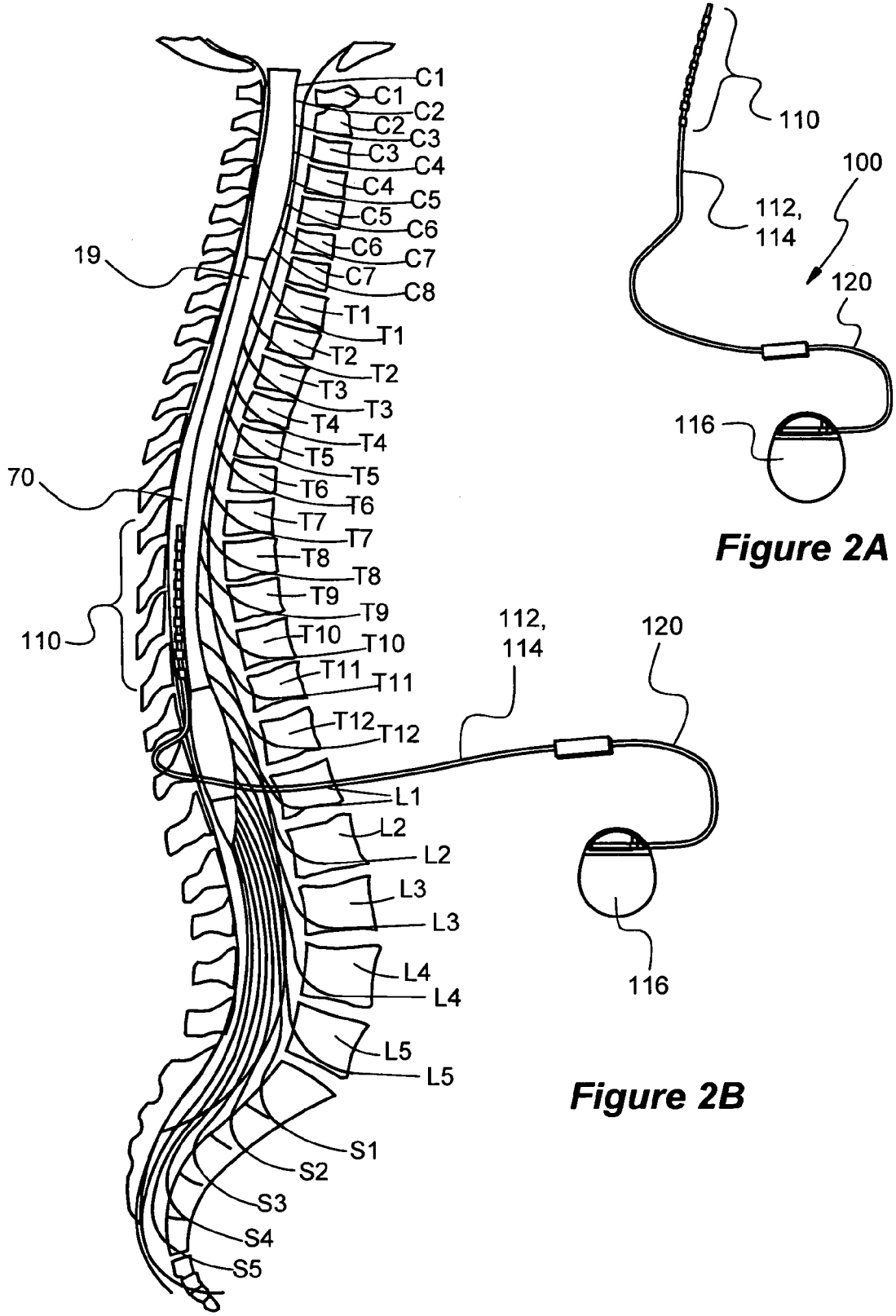
FIGS. 2A and 2B show a placement of the percutaneous lead for spinal cord stimulation with an in-line electrode array inserted alongside the spinal cord in the epidural space, in close proximity to the dura mater.
Figure 3A:
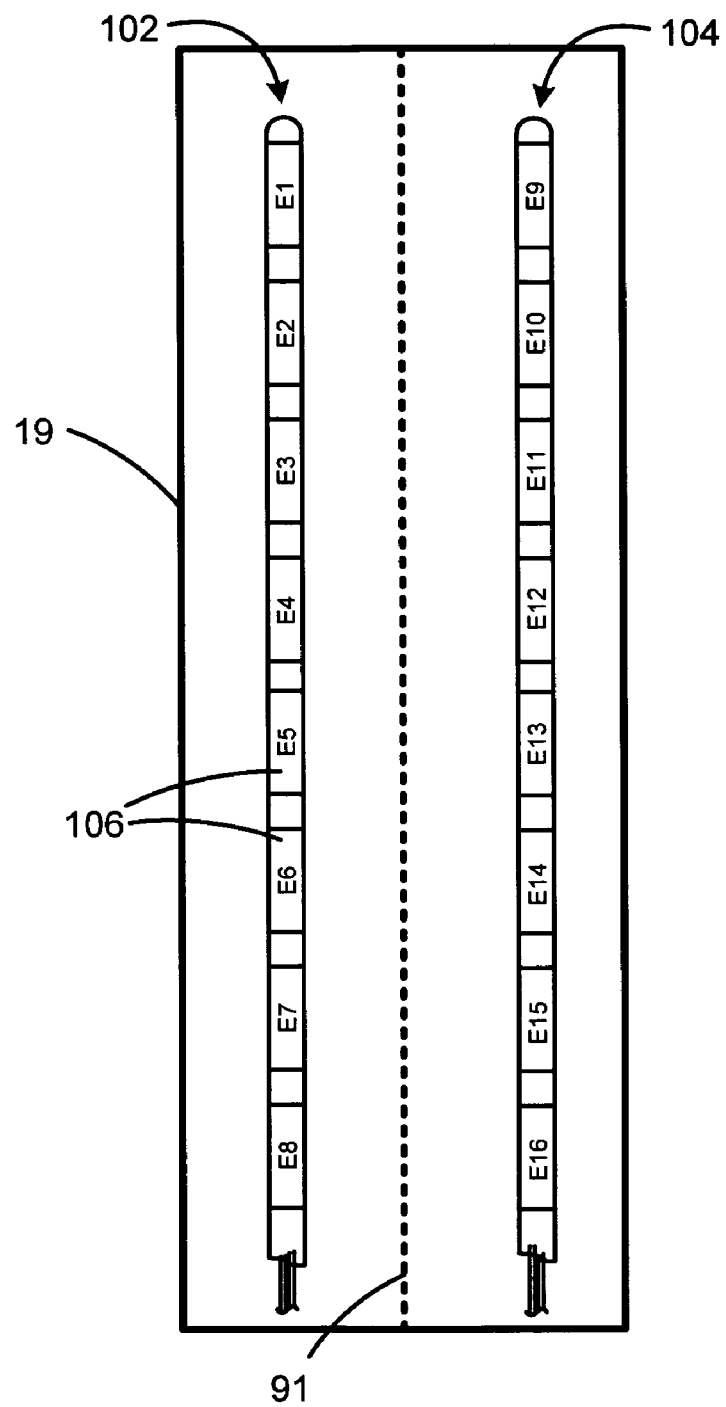
FIG. 3A and 3B show placement of two in-line electrode arrays on the left and right sides of the physiological midline of the spinal cord, respectively, in a perspective view and in cross-section.
Figure 3B:
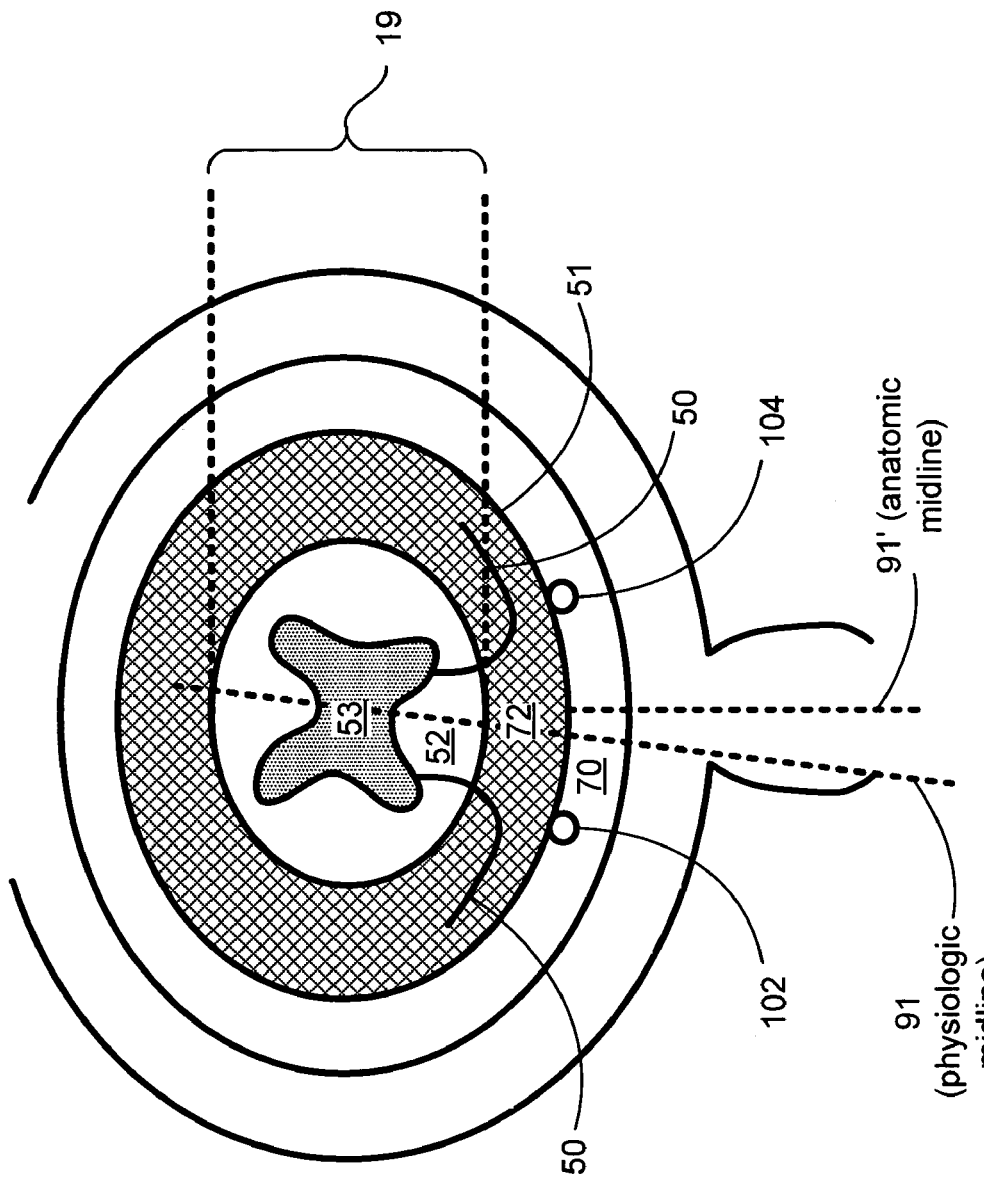
Figures 4, 5:
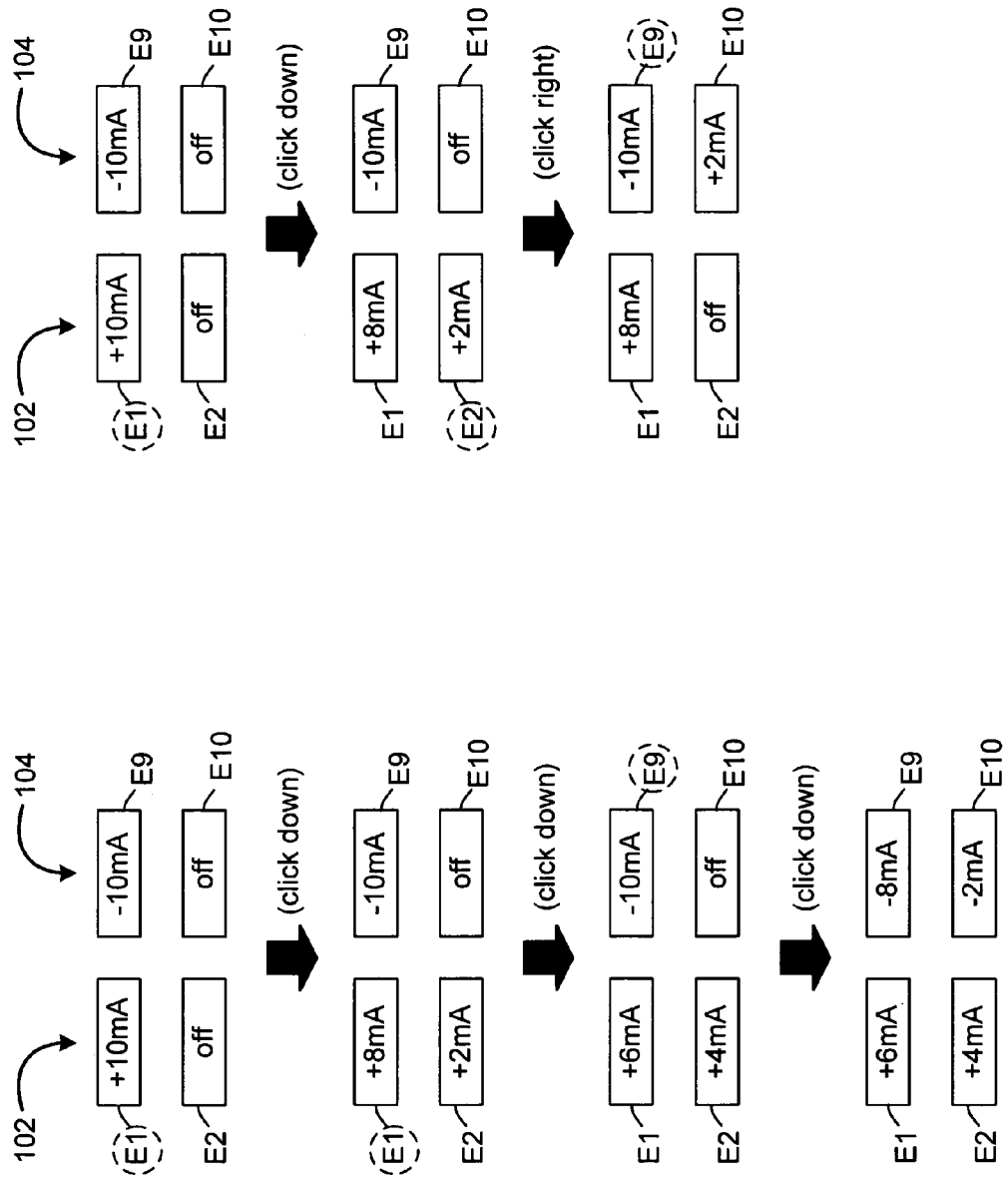
FIGS. 4 and 5 shows electrode current steering technique of the prior art.

Timing channels A and B in the simple example of FIG. 12 are respectively akin to the initial condition and final conditions discussed in the Background section of this disclosure. Because different timing channels are used, with no one electrode being simultaneously activated in the timing channels, the initial condition of timing channel A and the final condition of timing channel B can essentially be simultaneously tested (at least from the patient's point of view). Moreover, as will be made apparent later, such "simultaneous" testing of the conditions during set up can be accomplished much more quickly and efficiently than was possible in the prior art as illustrated in FIGS. 4-6. As also will be seen, the ability to "simultaneously" testing two different electrode conditions within two different timing channels allows for the electrodes to be tested and manipulated during set up with relative ease and without the potential for erroneous results.

In the embodiment of FIG. 12, such "simultaneous" testing of initial and final conditions is made possible by interleaving the pulses active in each timing channel. Thus, the pulses in timing channel B are activated at a time Ta-b after the pulses in timing channel A are activated. In this example, this means that the frequency, f, of the pulses in timing channel B is equal to the frequency of the pulses in timing channel A. Moreover, other stimulation parameters (pulse width, pulse amplitude) are the same as between the two channels, although this is not strictly required, especially as concerns pulse amplitude which will be discussed in further detail below. In short, and as will eventually be made clear, the stimulation parameters specified for the two (or more) timing channels can be wholly different, so long as no particular electrode is called upon to be simultaneously active in two different timing channels.

In a preferred embodiment, it is preferred that the time between pulses in the various timing channels, i.e., Ta-b or Th-a, be greater than or equal to 3 milliseconds. This is desired to allow for current recovery, be it passive (199') or through an active attempt to source/sink the same charge sunk/sourced from a particular electrode (not shown), as well as to allow the nerves time to recover between pulses.

Figure 13:
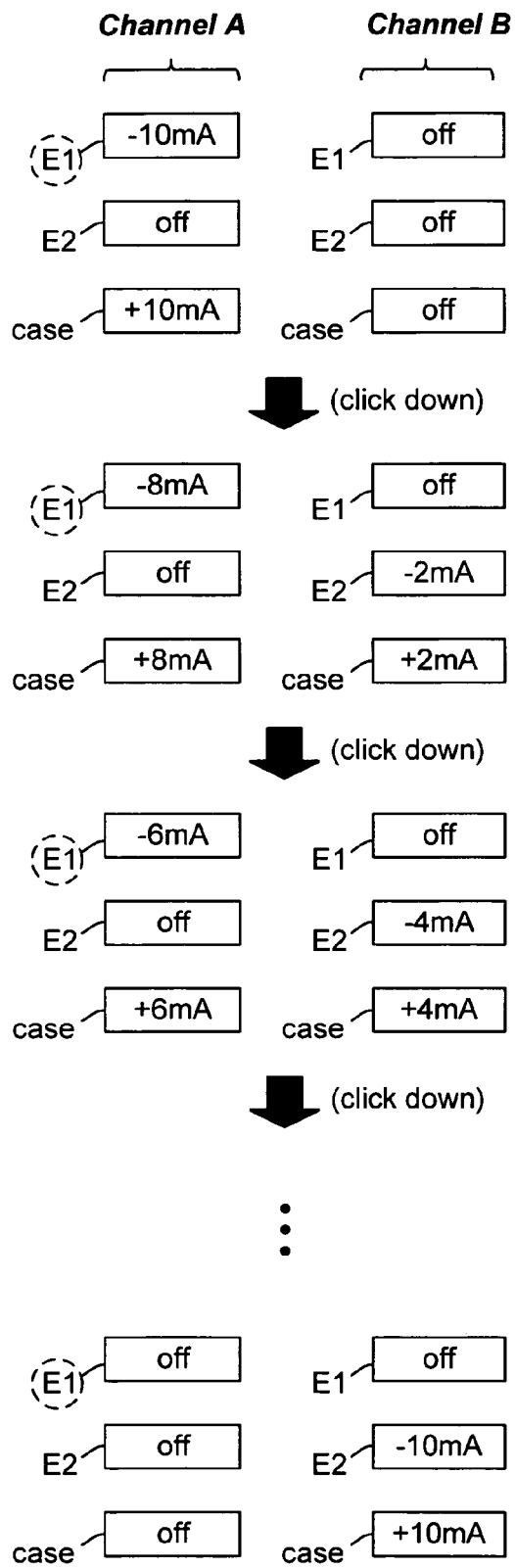
FIGS. 13 and 14 show simple examples of how current may be steered to new electrodes during set up using two timing channels.

FIG. 13 illustrates an embodiment of the disclosed use of multiple timing channels as applied to the Example of FIG. 12. In FIG. 13, the goal during set up is to move the initial conditions from FIG. 12 (E1/case) to the desired final conditions (E2/case) to see if such steering improves patient therapy. Accordingly, as before, the electrode to be steered (i.e., E1) is selected. When the patient or clinician uses an external programmer 202 or 204, such as a joystick or other directional device 206 (see FIG. 7), to move some portion of the current from electrode E1 to electrode E2, the current is so moved as FIG. 13 illustrates. However, this moved current appears in a different timing channel: whereas electrode E1's current was sourced in timing channel A, the moved current to electrode E2 is sourced in timing channel B. Subsequent downward clicks will move more of the of the current from E1 in timing channel A to E2 in timing channel B until, five clicks later in the example, the final conditions are reached in which all 10 mA of the source current is a transferred from electrode E1 to electrode E2.

It should be noted that the same "incremental" current movement approach is illustrated in FIG. 13 as was illustrated in the prior art. In other words, not all 10 mA of the E1's current was moved to E2 in timing channel B in one "click." For the reasons described earlier, such abrupt steering of all of the current in this manner could be at least uncomfortable for the patient. However, while an incremental approach is preferred for this reason, it is not strictly necessary, and the entirety of the current in timing channel A can be moved or duplicated in the second timing channel B in other useful embodiments. Moreover, as shown in the example of FIG. 13, the current transferred to electrode E2 in timing channel B is subtracted away from the current of electrode E1 in timing channel A, specifically, in 2 mA increments. However, this is not strictly necessary, and instead the full current (10 mA) can remain in timing channel A even as the current is gradually built up in electrode E2/timing channel B, as shown in the left half of FIG. 14. Thereafter, once the full current has been gradually established in electrode E2/timing channel B, the current in electrode E1/timing channel A can be gradually reduced, as shown in the right half of FIG. 14.

Figure 14:
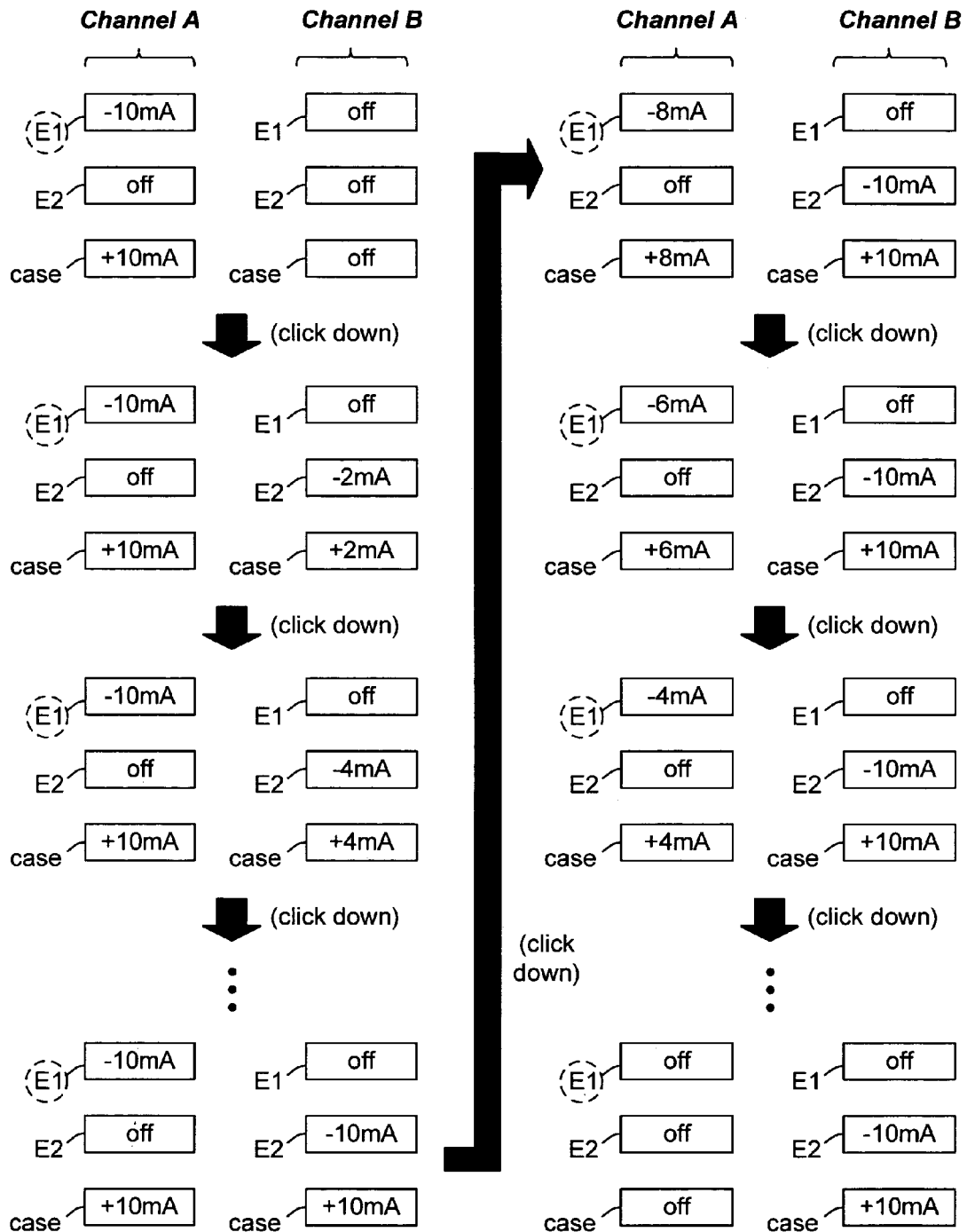

At this point, it can be appreciated even through the simple example of FIGS. 13 and 14 that the disclosed multi-channel set up technique has significant advantages when compared to the prior art. Significantly, the use of two timing channels allows two potentially-viable sets of stimulation parameters to be applied to the patient during set up in an interleaved fashion. So applied, the patient will independently feel the effects of both of the setting of both timing channels, but in a manner that does not blur the effect of two. By contrast, in the prior art, the gradual steering of current from E1 to E2 (continuing the current example) would inevitably involve intermediate states in which both E1 and E2 were simultaneously sourcing current in a signal timing channel. Such intermediary states, as noted earlier (see FIG. 6C, 11 1a), have the potential to recruit different nerves that would not be recruited in the initial (presumably good) and final (possibly even better) conditions. In other words, such intermediary conditions may inadvertently gravitate away from potentially useful therapy, and it is thus beneficial that embodiments of the disclosed technique do not involve such intermediary states.

Figure 6A:
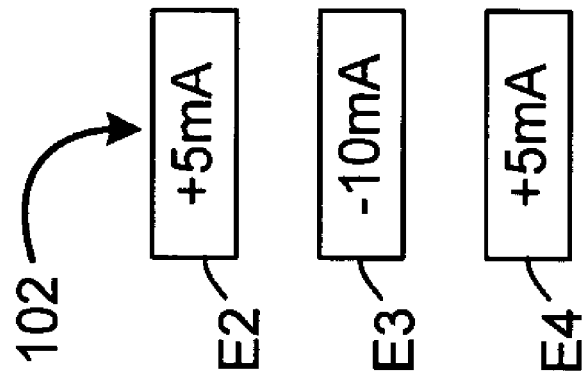
FIGS. 6A-6C show how current steering of FIGS. 4 and 5 could be used in the prior art to move electrode settings to new electrodes, albeit laboriously and with potential unsatisfactory results.
Figure 6B:
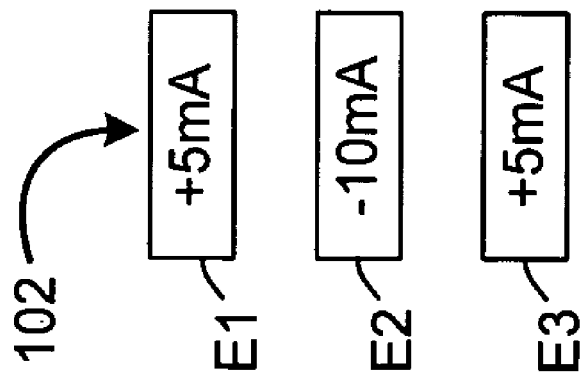
Figure 6C:
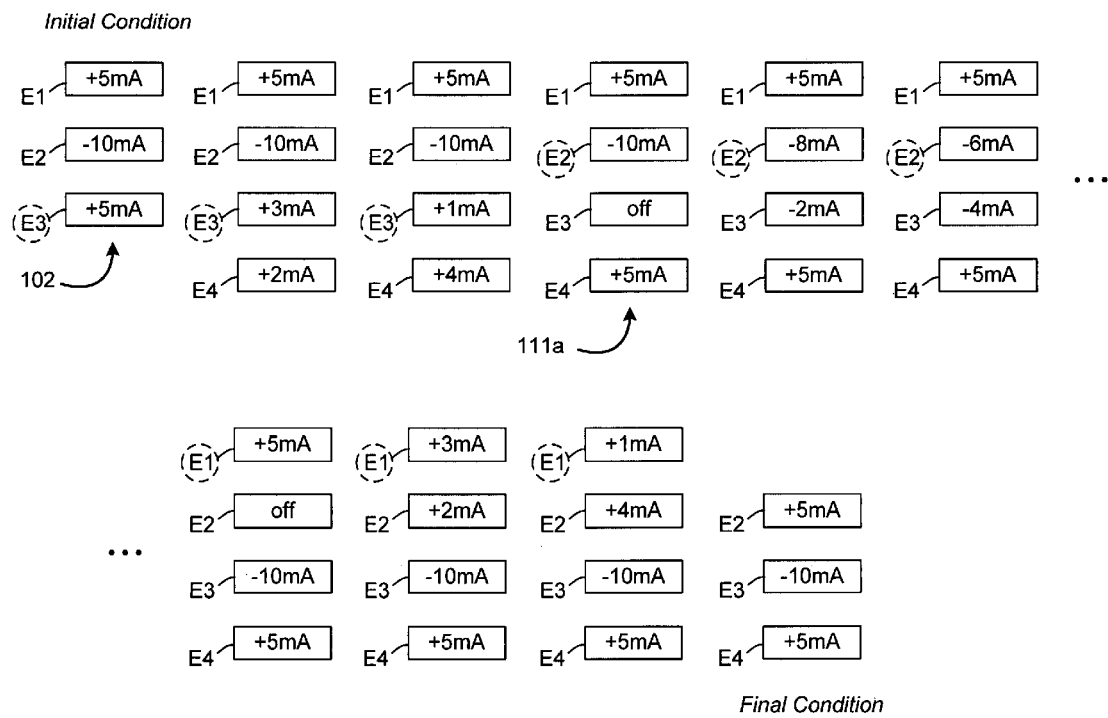
Figure 15:
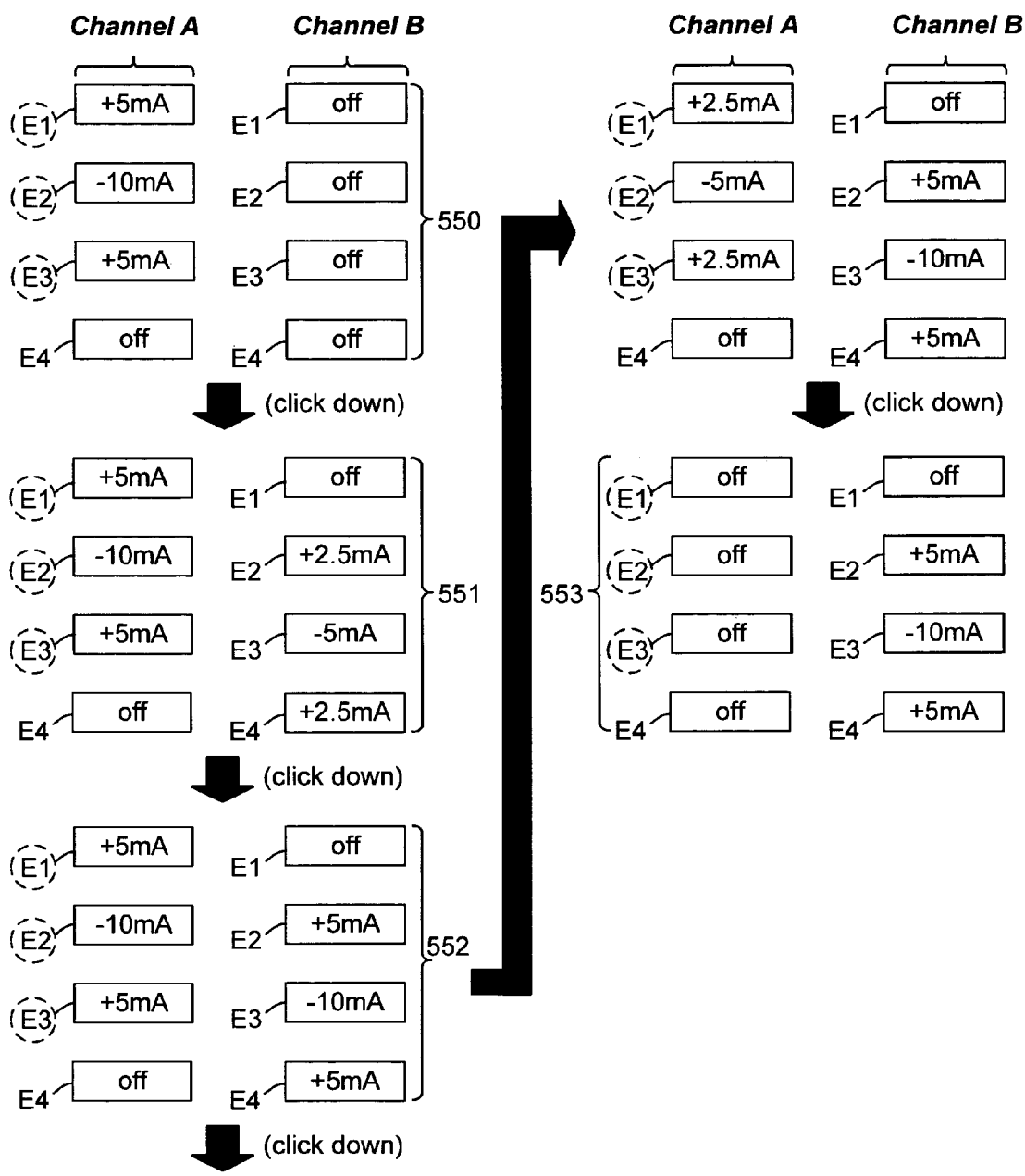
FIG. 15 shows how the example of FIG. 6C is more easily handled in accordance with an embodiment of the invention in which two timing channels are used during set up.

FIG. 15 illustrates an embodiment of the disclosed technique in the context of the example introduced earlier in FIG. 6. By way of review, the example of FIG. 6 involved shifting a tightly-group initial condition along a single lead 102 in which electrodes E1 and E3 each provide a 5 mA source current, while the middle electrode, E2, sinks the sum of that current, 10 mA (see FIG. 6A). As discussed earlier, during IPG set up, an assuming the initial conditions suggest generally satisfactory therapy to the patient, it might be desirable to shift this initial condition down the lead 102 to a final condition involving electrodes E2 to E4 (see FIG. 6B). Again by way of review, it was discussed that such shifting of the electrodes previously required many intermediary steps, so that the conditions of the various electrodes could be incrementally inch-wormed into position (see FIG. 6C). This approach was time consuming, and required passing though many intermediary steps not truly indicative of either the initial or desired final conditions (e.g., 111a, FIG. 6C), and therefore which might be perceived poorly by the patient.

As shown in FIG. 15, this example is much more easily and reliably handled using an embodiment of the disclosed multi-channel set up technique. As shown, the initial conditions (E1-E3; 550) are assumed. Once a plan has been formulated to switch the conditions to E2-E4, the patient or clinician can select the electrodes of interest, i.e., E1-E3 in this example, using an appropriate user interface as described earlier. Then, using (for example) the joystick or other directional device 206 (see FIG. 7), the user can click downward to move some of the current into electrodes associated with timing channel B. In this regard, it is assumed that timing channels A and B have already been somewhat pre-defined in their stimulation parameters, and that movement of the joystick operates to shift current to the new timing channel. For example, as a default, it may be the case that timing channel B has the same frequency and pulse width as in timing channel A. Moreover, the external programmer 202 or 204 may automatically set the delay between the pulses in the two timing channels (Ta-b and Tb-a) to be equal, such that the pulses in timing channel B are positioned exactly in the middle of the pulses of timing channel A. Of course, Ta-b and Th-a need not be equal, and this suggestion is therefore merely exemplary. The important thing in setting the timing of the pulses is to ensure that the pulses in the two timing channels do not interfere with each other. Hence, some minimal amount of time is advisable (e.g., 3 ms) to allow for current and nerve tissue recovery, for example. Ultimately, programming the parameters of the various timing channels during set up and the operation of the joystick can be accomplished with the assistance of one of the external programmers such as HHP 202 or CP 204 (see FIG. 7).

Once the system is enabled to handle at least two timing channels during set up, and once the electrodes to be manipulated are selected, adjustment of the electrodes can occur as shown in FIG. 15. As shown, clicking down on the joystick represents movement of some amount of current to new electrodes in timing channel B. Thus, as shown, upon the first click, an incremental amount of current is preferably placed on the final condition electrodes (E2-E4) (551) in timing channel B. (In this example, and as is different compared to earlier examples, the increment of current used is 2.5 mA for ease of illustration, although of course no particular increment of current is important to any embodiment of the invention). As depicted in FIG. 15, establishment of current in timing channel B does not immediately affect the amount of current in the initial conditions of timing channel A, similarly to the left side of FIG. 14. (This is different from the example of FIG. 13, in which current was subtracted from timing channel A and added to timing channel B, amounting in a constant amount of current when the two channels were summed). Subsequent clicks increase the incremental current, until the amount of the current on the final condition electrodes in timing channel B (E2-E4) matches that of the initial condition electrodes in timing channel A (E1-E3) (552). Further subsequent clicks then incrementally remove the current from the initial condition electrodes in timing channel A, which eventually leaves as active only the final condition electrodes in timing channel B (553).

At this point, timing channel B, the only currently active timing channel, can be viewed as or reset to the primary timing channel, such that further use of the method will work to move some amount of current back to electrodes in timing channel A, or to electrodes in another new timing channel C, etc. Moreover, use of the disclosed technique can also be used with the prior art technique. In other words, the patient or clinician using HHP 202 or CP 204 can program the IPG during set up such that steering the current will involved physical movement along the electrode array 110 in one timing channel, or will move current to a new timing channel. Because it may still be useful to move current in both of these types of ways, embodiments of the invention may indeed use both ways.

As can be seen from FIG. 15, movement from the initial conditions to the final conditions is greatly facilitated when compared to the technique of the prior art (FIG. 6C). Moreover, and as noted previously, the disclosed technique does not suffer from the same problem of intermediary steps during which the electrodes are really not indicative of either the initial or final conditions (FIG. 6C, 111a), and which may discourage the patient or clinician during set up away from useful optimization for the electrodes.

It should be noted that in useful embodiments of the disclosed multi-channel set up technique, the pulse amplitudes (i.e., current) in the various timing channels can be affected differently from what is illustrated in the various examples. For example, the amount that current is incremented or decremented in the various active electrodes in the various timing channels can vary and need not be a set value. For example, larger increments can be used in initial steps, with smaller increments used as various target conditions are approached.

Also, amplitude adjustment may be made independently of the use of the disclosed technique. For example, it cannot be assumed in FIG. 15 that the total source current of the initial condition electrodes (10 mA) would be optimal when applied to the final condition electrodes. After all, differing electrodes will recruit different nerves with different thresholds, and therefore may require different pulse amplitudes to achieve the same basis therapeutic effect (e.g., paresthesia). Accordingly, other traditional pulse amplitude (i.e., current) adjustment mechanisms (not shown) can also be used in conjunction with the disclosed technique. For example, after performing the steps as shown in FIG. 15 (e.g., after 553), or even at some intermediary step, it may be advisable to globally adjust the currents. For example, after completing the steps as shown in FIG. 15, it may be advisable to adjust the total source current from its initial value of 10 mA to higher (e.g., 12 mA) or lower (e.g., 8 mA) values. Such traditional means of adjusting the current would employ programming of the HHP 202 or CP 204 (FIG. 7) as is well known.

The disclosed technique can involve other stimulation parameters changes as well. For example, during performance of the steps in FIG. 15, the frequency of the pulses can be made to change. For example, if the initial condition frequency of the pulses (550) is f, intermediary steps (551) could take place at 0.75 f, while the middle step (552) occurs at 0.5 f. Such adjustment (lowering) of the frequency would be sensible at step 552, as the conditions at that point (absent adjustment) are essentially equivalent to a stimulation frequency of 2 f (albeit with different electrodes). As the steps continue (e.g., to 553), the frequency can gradually be brought back down to f.

It should be understood that reference to an "electrode on the implanted stimulator device" includes electrodes on the implantable stimulator device, or the electrodes on the associated electrode leads, or any other structure for directly or indirectly stimulating tissue.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method for adjusting electrodes during set up of a stimulator device, comprising:
   defining a first timing channel which provides a first set of stimulation pulses to at least one electrode on the stimulator device;
   defining at least one second timing channel which provides at least a second set of stimulation pulses to at least one electrode on the stimulator device, wherein the first and second sets of pulses are non-overlapping in the first and second timing channels; and
   gradually transitioning from activating the first set of stimulation pulses to activating the second set of stimulation pulses by gradually increasing a magnitude of the second set of stimulation pulses while maintaining a first magnitude of the first set of stimulation pulses, and once the second set of stimulation pulses increases to a second magnitude, gradually decreasing a magnitude of the first set of stimulation pulses while maintaining the second magnitude of the second set of stimulation pulses.

2. The method of claim 1, wherein the first and second sets of pulses have the same frequency.

3. The method of claim 1, wherein the first and second timing channels define which electrodes act as source or sink electrodes.

4. The method of claim 1, wherein gradually increasing the magnitude of the second set of stimulation pulses comprises incrementally adding to an amplitude of the second set of stimulation pulses.

5. The method of claim 1, wherein gradually the first set of stimulation pulses comprises incrementally subtracting from an amplitude of the first set of stimulation pulses.

6. The method of claim 1, further comprising using a programmer external to the stimulator device to gradually transition from activating the first set of stimulation pulses to activating the second set of stimulation pulses.

7. The method of claim 1, wherein the stimulator is implanted within a patient.

8. A stimulation system comprising:
   an implantable stimulator device configured for conveying a first set of stimulation pulses within a first timing channel to at least one electrode, and for conveying a second set of stimulation pulses within a second timing channel to at least one electrode, wherein the first and second sets of pulses are non-overlapping in the first and second timing channels; and
   an external programmer configured for gradually transitioning from activating the first set of stimulation pulses to activating the second set of stimulation pulses by gradually increasing a magnitude of the second set of stimulation pulses while maintaining a first magnitude of the first set of stimulation pulses, and once the second set of stimulation pulses increases to a second magnitude, gradually decreasing a magnitude of the first set of stimulation pulses while maintaining the second magnitude of the second set of stimulation pulses.

9. The stimulation system of claim 8, wherein the first and second sets of pulses have the same frequency.

10. The stimulation system of claim 8, wherein the first and second timing channels define which electrodes act as source or sink electrodes.

11. The stimulation system of claim 8, wherein gradually increasing the magnitude of the second set of stimulation pulses comprises incrementally adding to an amplitude of the second set of stimulation pulses.

12. The stimulation system of claim 8, wherein gradually decreasing the magnitude of the first set of stimulation pulses comprises incrementally subtracting from an amplitude of the first set of stimulation pulses.

* * * * *